(12) United States Patent
Kitamura et al.

(10) Patent No.: US 11,330,992 B2
(45) Date of Patent: May 17, 2022

(54) HEIGHT CORRECTION DEVICE, AND HEIGHT CORRECTION METHOD AND BLOOD PRESSURE MEASUREMENT SYSTEM USING HEIGHT CORRECTION DEVICE

(71) Applicants: OMRON CORPORATION, Kyoto (JP); OMRON HEALTHCARE CO., LTD., Kyoto (JP)

(72) Inventors: Yumi Kitamura, Kyoto (JP); Takahide Tanaka, Kyoto (JP); Shingo Yamashita, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 342 days.

(21) Appl. No.: 16/553,344

(22) Filed: Aug. 28, 2019

(65) Prior Publication Data
US 2019/0387978 A1    Dec. 26, 2019

Related U.S. Application Data

(63) Continuation of application No. PCT/JP2018/009561, filed on Mar. 12, 2018.

(30) Foreign Application Priority Data

Mar. 15, 2017    (JP) .............................. JP2017-050218

(51) Int. Cl.
*A61B 5/022*    (2006.01)
*A61B 5/021*    (2006.01)
(Continued)

(52) U.S. Cl.
CPC .............. *A61B 5/022* (2013.01); *A61B 5/021* (2013.01); *A61B 5/02141* (2013.01);
(Continued)

(58) Field of Classification Search
CPC ..... A61B 5/022; A61B 5/021; A61B 5/02141; A61B 5/02225; A61B 5/1072;
(Continued)

(56) References Cited

U.S. PATENT DOCUMENTS

2007/0028684 A1    2/2007 Benz
2010/0160793 A1    6/2010 Lee et al.
(Continued)

FOREIGN PATENT DOCUMENTS

CN    101238358    8/2008
CN    106456019    2/2017
(Continued)

OTHER PUBLICATIONS

International Search Report dated May 29, 2018 in International (PCT) Application No. PCT/JP2018/009561 with English translation.

(Continued)

*Primary Examiner* — Sean P Dougherty
*Assistant Examiner* — Kyle W. Kretzer
(74) *Attorney, Agent, or Firm* — Wenderoth, Lind & Ponack, L.L.P.

(57) ABSTRACT

A height correction device measures height information on the reference position of the heart and height information on the wrist to which a blood pressure measurement device is attached using communication technology when the body of a subject rotates or moves at the position where the measurement device is attached during the measurement period including the sleep period, subjects the obtained blood pressure measurement values to height correction using height information, and approximates the obtained blood pressure measurement values to blood pressure measurement values measured at the reference position of the heart, to thereby obtain highly accurate measurement values.

7 Claims, 7 Drawing Sheets

(51) Int. Cl.
*A61B 5/00* (2006.01)
*A61B 5/107* (2006.01)
(52) U.S. Cl.
CPC ......... *A61B 5/0024* (2013.01); *A61B 5/02225* (2013.01); *A61B 5/1072* (2013.01); *A61B 5/681* (2013.01); *A61B 5/6804* (2013.01); *A61B 5/742* (2013.01)
(58) Field of Classification Search
CPC ..... A61B 5/0024; A61B 5/6804; A61B 5/681; A61B 5/742; A61B 5/7203; A61B 5/1113; A61B 5/1114
See application file for complete search history.

(56) References Cited

U.S. PATENT DOCUMENTS

| | | | | |
|---|---|---|---|---|
| 2010/0179439 | A1* | 7/2010 | Kuschel | A61B 5/022 600/485 |
| 2015/0327784 | A1 | 11/2015 | Lading et al. | |
| 2016/0029904 | A1* | 2/2016 | Quinn | A61B 5/0024 600/499 |
| 2016/0198977 | A1* | 7/2016 | Eom | A61B 5/02416 600/384 |

FOREIGN PATENT DOCUMENTS

| | | |
|---|---|---|
| JP | 8-215161 | 8/1996 |
| JP | 2006-102190 | 4/2006 |
| JP | 2007-54648 | 3/2007 |
| JP | 3140916 | 4/2008 |
| JP | 2014-68825 | 4/2014 |

OTHER PUBLICATIONS

Journal of the Society of Instrument and Control Engineers, vol. 48, No. 7, pp. 560-564, non-official translation (Ootsuki, Tomoaki, Wireless Communication Technology for Measurement and Control) cited in International Search Report.

International Preliminary Report on Patentability dated Sep. 19, 2019 in corresponding International (PCT) Patent Application No. PCT/JP2018/009561.

Decision to Grant dated Aug. 9, 2021 in corresponding Chinese Application No. 201880017592.4 with English translation.

Simi Susan Thomas et al., "BioWatch: A Non-Invasive Wrist-Based Blood Pressure Monitor that Incorporates Training Techniques for Posture and Subject Variability", IEEE Journal of Biomedical and Health Informatics, Jul. 2015, pp. 1-10.

* cited by examiner

HEIGHT CORRECTION DEVICE, AND HEIGHT CORRECTION METHOD AND BLOOD PRESSURE MEASUREMENT SYSTEM USING HEIGHT CORRECTION DEVICE

CROSS-REFERENCE TO RELATED APPLICATIONS

This is a Continuation Application of PCT Application No. PCT/JP2018/009561, filed Mar. 12, 2018, and based upon and claims the benefit of priority from the Japanese Patent Application No. 2017-050218, filed Mar. 15, 2017, the entire contents of all of which are incorporated herein by reference.

FIELD

The present invention relates to a height correction device that performs height correction to reduce the influence which the gravity may have on measurement values obtained from a measurement device, and to a blood pressure measurement system and a height correction method using the height correction device.

BACKGROUND

Conventionally, physical information for use in diagnosis has been acquired using various measurement devices. For example, in blood pressure measurement, a blood pressure measurement device is wound around a subject's upper arm and a blood pressure is measured in this state, but in recent years, a small-sized wrist type blood pressure measurement device to be attached to the wrist (forearm) is also used. Even if the measuring device is smaller in size, the information obtained by using it is required to be more accurate.

Concerning the blood pressure measurement, blood pressure is affected by the gravity as disclosed in Patent Document 1, and it has been confirmed that a measurement error can be reduced by performing measurement at a height close to the heart (see Jpn. Pat. Appln. KOKAI Publication No. 2007-54648). For this reason, it is preferable that the wrist type blood pressure measurement device is also worn at the same height as the heart at the time of measurement. If the measurement period is short, there would be no problem, but if the measurement is continuously performed for a long time or if the measurement is performed at regular intervals, it is not easy to keep the wrist at the position of the heart. Therefore, as a commercially available device for correcting the height difference of a measurement position, a height correction sensor using the water head pressure of a liquid in a sealed tube is additionally employed, and height correction is made on measurement values.

SUMMARY

A height correction device according to a first aspect and a eighth aspect of the present invention includes a reference position transmitter that transmits a first position information signal indicative of a predetermined reference position of a subject, an attachment position transmitter that transmits a second position information signal indicative of an attachment position of an external measurement device attached to the subject, a first sensor that detects a variation in the reference position, a second sensor that detects a variation in the position of the measurement device, a first receiver that receives the first position information signal and the second position information signal, a second receiver that receives the first position information signal and the second position information signal, and that is spaced apart from the first receiver by a predetermined distance in a direction of gravity, a height information generation unit that obtains a height of the reference position from the first position information signal, that obtains the position of the measurement device from the second position information signal, and that calculates a height difference between the reference position and the position of the measurement device, a height correction value calculation unit that calculates a height correction value for approximating a measurement value measured at the position of the measurement device to a measurement value measured at the reference position, and a processing unit that calculates the height difference and updates the height correction value each time a height variation is detected by the first sensor and the second sensor, and that corrects a measurement value measured by the measurement device in accordance with the height correction value.

The height correction device according to a second aspect includes a reference position transmitter that transmits a first position information signal indicative of a position of a heart, an attachment position transmitter that transmits a second position information signal indicative of an attachment position of an external blood pressure measurement device, a first sensor that detects a variation in a height of the position of the heart, a second sensor that detects a variation in a height of the position of the blood pressure measurement device, a first receiver that receives the first position information signal and the second position information signal, a second receiver that receives the first position information signal and the second position information signal, and that is spaced apart from the first receiver by a predetermined distance in a direction of gravity, a height information generation unit that obtains the height of the position of the heart from the first position information signal, that obtains a height of the attachment position of the blood pressure measurement device from the second position information signal, and that calculates a height difference between the position of the heart and the attachment position, a height correction value calculation unit that calculates a height correction value to correct a blood pressure measurement error caused by action of the gravity due to the height difference, a memory unit that stores the height correction value calculated by the height correction value calculation unit and a processing unit that calculates the height difference and updates the height correction value each time a height variation is detected by the first sensor and the second sensor, and that corrects a blood pressure measurement value measured by the blood pressure measurement device in accordance with the height correction value.

The height correction device according to a third aspect forms two triangles such that the first receiver is a first vertex, one of the attachment position transmitter and the attachment position transmitter is a second vertex, and a second receiver is a third vertex, wherein the height information generation unit calculates distance information from the first receiver and the second receiver to the reference position transmitter, using the triangle, and generates a height difference between the heart and the blood pressure measurement device from coordinate information based on the distance information.

The height correction device according to a fourth aspect further includes a measurement timing setting unit that causes the blood pressure measurement device to perform blood pressure measurement at a timing after elapse of a predetermined body movement detection standby time, after the height difference is calculated and the height correction value is updated.

The measurement timing setting unit of the height correction device according to a fifth aspect sets blood pressure measurement which is to be irregularly performed by the blood pressure measurement device immediately after the height correction value is updated in addition to the blood pressure measurement which the blood pressure measurement device performs in time series at regular intervals within a preset measurement period.

The first sensor and the reference position transmitter of the height correction device according to a sixth aspect are used at least in pairs, and the height correction device according to a sixth aspect further includes a belt that is wound around the subject, and an attachment device that is movably provided on the belt and that enables the first sensor and the reference position transmitter to be attached.

The height correction device according to a seventh aspect further includes a first communication unit that is connected to the first sensor and the reference position transmitter, and that converts a body movement occurrence signal detected by the first sensor and an instruction signal instructing the reference position transmitter to transmit a reference position signal into wireless signals for wireless communications, a second communication unit that is connected to the blood pressure measurement device, the second sensor and the reference position transmitter, and that converts a measurement timing signal for the blood pressure measurement device, a body movement occurrence signal detected by the second sensor and an instruction signal instructing the attachment position transmitter to transmit an attachment position signal into wireless signals for wireless communications, and a main communication unit that performs wireless communications between the first communication unit and the second communication unit, and that communicates the body movement occurrence signal, the reference position signal and the attachment position signal with the measurement timing setting unit.

The height correction method according to an eighth aspect includes transmitting a height of a reference position as a first position information signal, transmitting a height of an attachment position of an external measurement device as a second position information signal, detecting a variation in the reference position, detecting a variation in the position of the measurement device, receiving the first position information signal and the second position information signal as first reception signals, receiving the first position information signal and the second position information signal as second reception signals at a position that is away from a reception position of the first reception signals by a predetermined distance in a direction of gravity, obtaining a height of the reference position from the first position information signal, obtaining the position of the measurement device from the second position information signal, and calculating a height difference between the reference position and the position of the measurement device, calculating a height correction value for approximating a measurement value measured at the position of the measurement device to a measurement value measured at the reference position, and calculating the height difference and updating the height correction value each time a variation in the height of the reference position and in a height of the position of the measurement device is detected, and correcting a measurement result measured by the measurement device in accordance with the height correction value, so as to approximate the measurement result to a measurement result measured at the height of the reference position.

According to the first aspect, where a subject portion to which the external measurement device is attached moves relative to a reference position of the subject, a height difference between the reference position and the portion to which the measurement device is attached is calculated, a height correction value is determined from the height difference, and a measured measurement value is corrected such that it is approximated to a measurement value measured at the reference portion, to thereby obtain a highly accurate measurement value.

According to the second aspect, where the body of a supine subject rotates or moves at a measurement device attachment position during the measurement period including the sleep period, height information on a measurement reference position of the body and height information on the device attachment position are measured, and an obtained measurement value is subjected to height correction using the height information and is approximated to a measurement value measured at the height of the measurement reference position to thereby obtain a highly accurate measurement value.

Furthermore, according to the second aspect, even if the subject unconsciously rolls over or swings an arm in the sleep state, a height correction value is updated to a new height correction value, and a measurement value obtained by the blood pressure measurement device is always corrected and approximated to a blood pressure value obtained at the height of the heart, so that a measurement error is reduced and an accurate blood pressure value can be obtained. Every time the body moves, blood pressure measurement is performed after the end of the movement. It is therefore possible to clearly confirm whether the change in blood pressure value is due to the body movement or due to a reason other than the body movement. Thus, misdiagnosis can be eliminated and blood pressure values can be made to contribute to accurate diagnosis. In the height correction device, the measurement unit including the body movement sensor and the transmitter can be integrated with the blood pressure measurement device, so that the height correction device can be easily attached to or detached from such a portion of the subject as the wrist.

According to the third aspect, two triangles are formed such that the first receiver, the attachment position transmitter or the reference position transmitter and the second receiver are vertices, distance information from the first receiver and second receiver to the reference position transmitter is calculated using the triangulation technique and sine theorem. Based on the coordinate information obtained from the distance information, a height difference between the heart and the blood pressure measurement device can be generated.

According to the fourth aspect, after a body movement of the subject is detected and the body movement detection standby time set in advance elapses, a height correction value is calculated and a blood pressure is measured. Therefore, even if the subject causes a body movement discontinuously, calculation processing of the height correction value is not performed provided that the body movement is within the body movement detection standby time. Therefore, unnecessary blood pressure measurement is not performed, and unnecessary power consumption is prevented.

According to the fifth aspect, blood pressure measurement values that are obtained by the blood pressure measurement performed after a body movement of the subject occurs and the height correction value is updated are recorded between blood pressure measurement values which the blood pressure measurement device acquires in time series and at regular intervals, i.e., predetermined intervals which the blood pressure measurement device sets in advance. Since the measurement result is as such, it can be confirmed at which time (a point of time) the body movement occurs.

According to the sixth aspect, a belt or vest that is provided with at least two attachment devices to which second measurement units are removably attached, and which are movable on the belt, is wound around the chest of the subject. Since the at least two second measurement units can be moved in accordance with the physical constitution of the subject, they can be properly positioned near the heart, and attachment and detachment are easy.

According to the seventh aspect, the first measurement unit and second measurement unit worn on the body (chest and wrist) of the subject communicate transmission instructions and position information signals by wireless. Since the height correction device has a cordless configuration which does not employ signal lines, all factors that disturb the movement of the subject are eliminated. Even if measurement is performed for a long time, an uncomfortable feeling is not caused during operation due to signal lines, and the feeling of discomfort can be remarkably reduced.

DETAILED DESCRIPTION

Where the above-described wrist type blood pressure measurement device is used for blood pressure measurement performed for a long time, and if the subject moves the wrist at the time of measurement, the accuracy of the measured blood pressure value is affected. With regard to whether or not the accuracy is affected, the person who makes diagnosis or the measurer should look at the state of measurement on the spot. If not, it is difficult to determine whether a change in the blood pressure value is produced actually in the subject or if it is attributable to the body movement caused by a wrist movement. In particular, even if the subject's body rotation or the movement of the wrist affects the measured blood pressure value in an unconscious state, as in the case where the subject rolls over during sleep, the person who makes diagnosis cannot easily determine whether or not the blood pressure measurement value is affected by merely looking at the measurement value.

The wrist type blood pressure measurement device is of a type that incorporates a battery. Therefore, if it is used for continuous measurement performed for a long time, the capacity of the battery should be increased to secure sufficient consumption power. Since this causes an increase in the weight of the device or an increase in the size of the casing, the increase of the capacity is not preferable from the viewpoint of weight reduction and downsizing.

In addition, if the blood pressure measurement period extends into the sleep time, the height correction sensor described above may be used, but since the tube is attached and fixed such that it extends from the vicinity of the heart to the wrist, there is a possibility that a load restricting the unconscious body movement may be applied to the subject, causing a feeling of discomfort and giving rise to stress such as an absence of sleep.

Accordingly, an object of the present invention is to provide a height correction device which obtains height information using a set measurement reference portion and performs height correction on a measured blood pressure value if the body of a subject to whom blood pressure measurement is performed moves, and which approximates the measured blood pressure value to a measurement value obtained at the height of the measurement reference portion to thereby obtain a highly accurate measurement value, and also to provide a blood pressure measurement system and a height correction method using the height correction device.

Embodiments of the present invention will be described in detail with reference to the accompanying drawings.

[First Embodiment]

Figure 1:
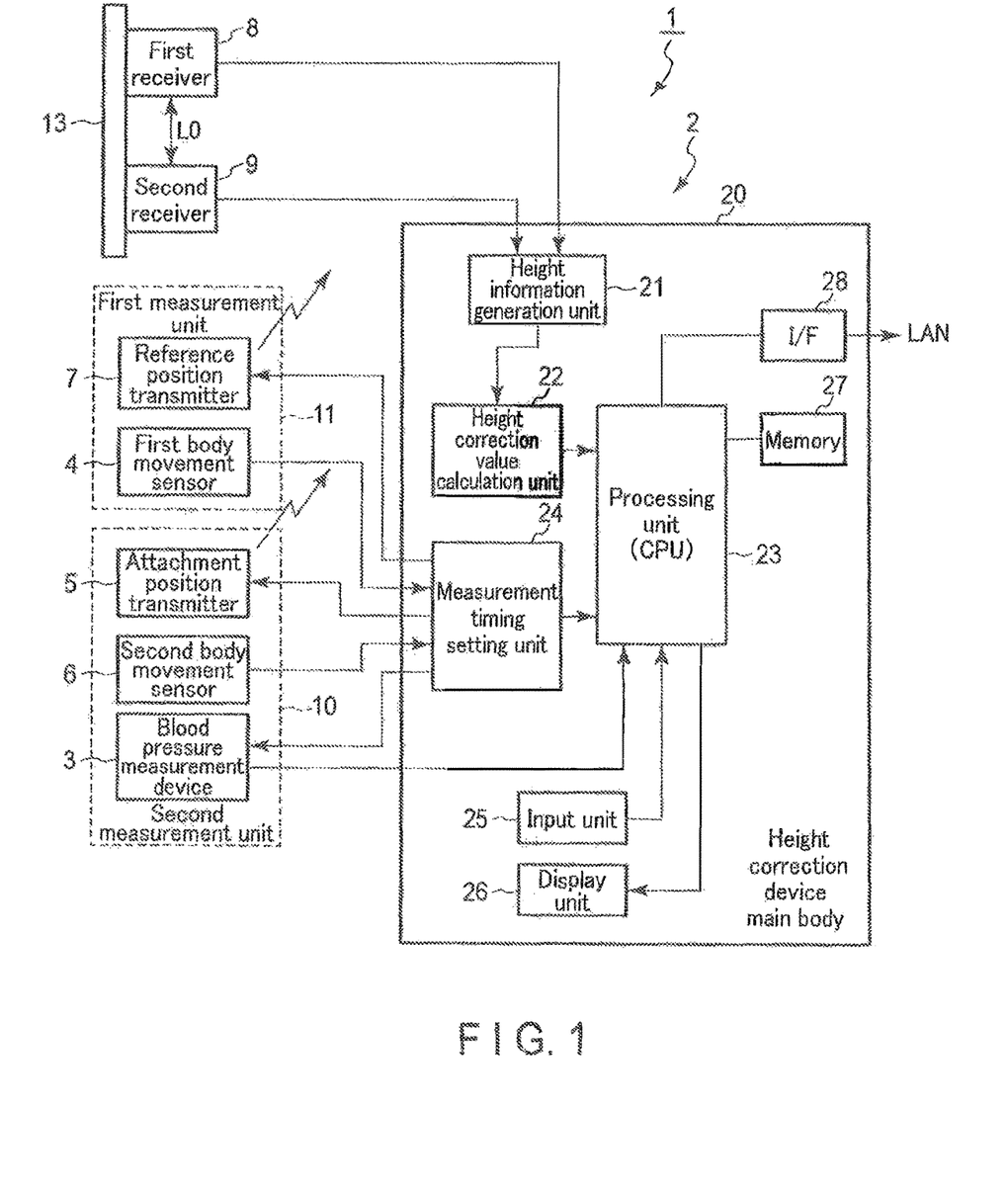
FIG. 1 is a block diagram showing a configuration example of a blood pressure measurement system that uses a height correction device according to a first embodiment.
Figure 2:
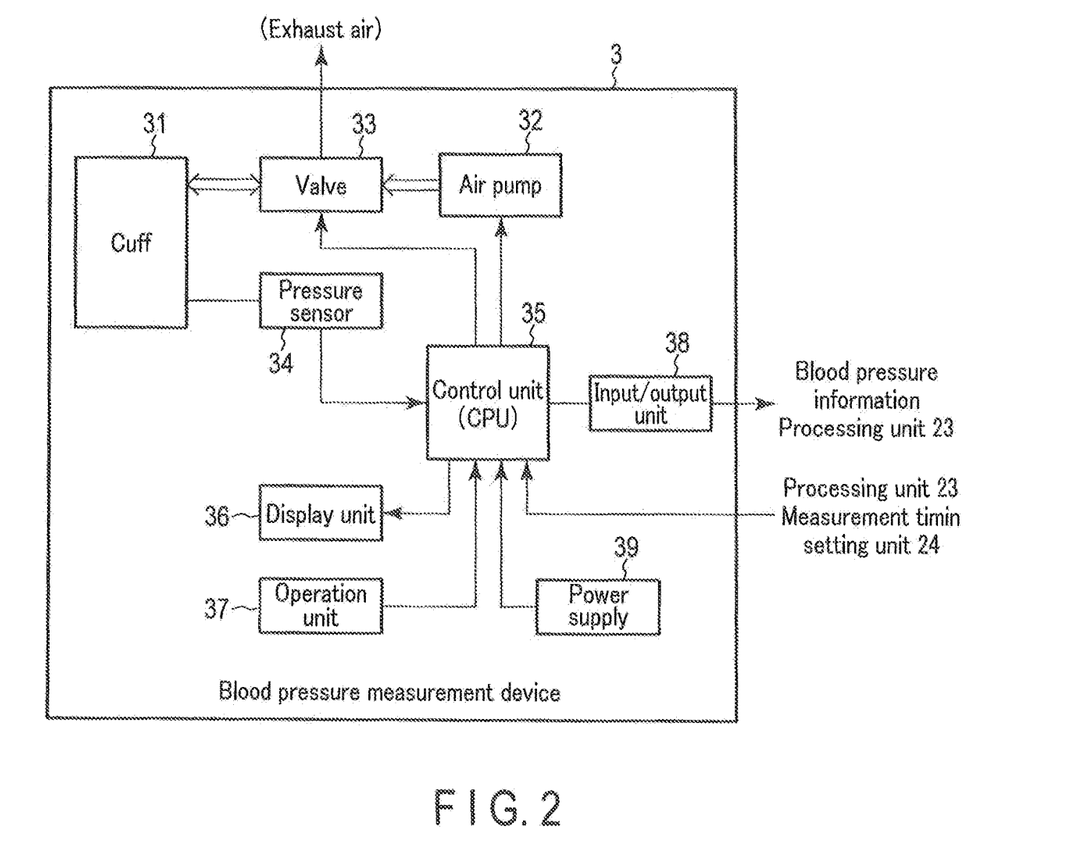
FIG. 2 is a block diagram showing a configuration example of a wrist-worn type blood pressure measurement device of the blood pressure measurement system.
Figure 3:
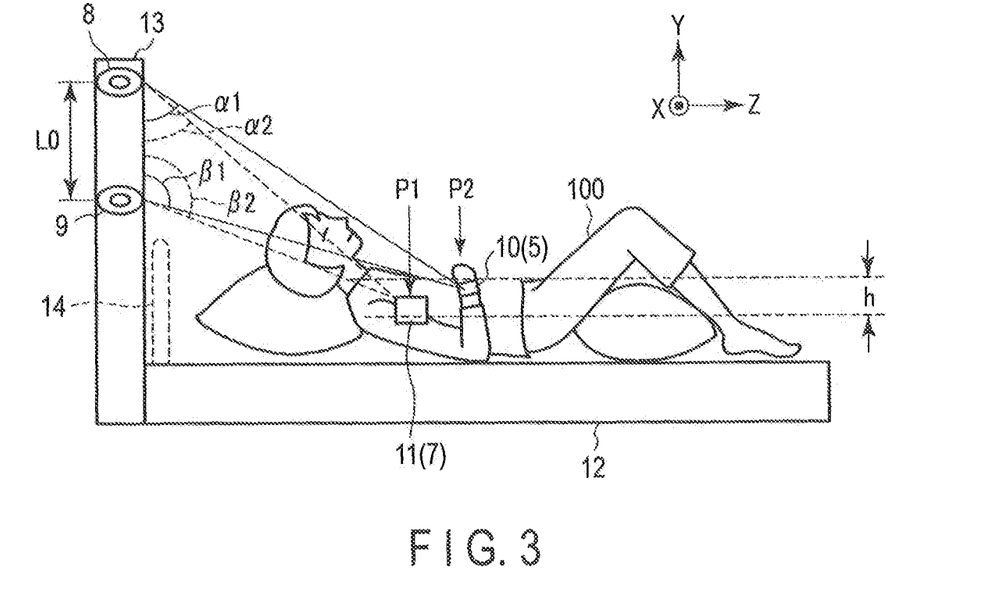
FIG. 3 is a diagram conceptually showing the arrangement positions of a transmitter and a receiver.
Figure 4:
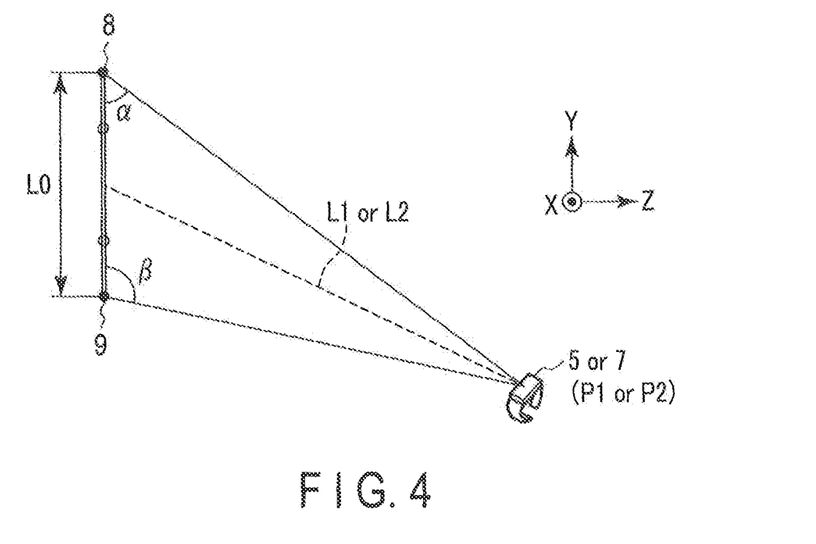
FIG. 4 is a diagram showing a concept for calculating a distance to a blood pressure measurement device or a heart position or coordinates thereof, using triangulation according to the present embodiment.

A blood pressure measurement system using a height correction device according to the first embodiment of the present invention will be described. FIG. 1 is a block diagram showing a configuration example of the blood pressure measurement system 1 using the height correction device according to the first embodiment. FIG. 2 is a block diagram showing a configuration example of a wrist-worn type blood pressure measurement device of the blood pressure measurement system. FIG. 3 is a diagram conceptually showing the arrangement positions of a transmitter and a receiver. FIG. 4 is a conceptual diagram for illustrating how the distance to the blood pressure measurement device or a heart position or coordinates thereof are calculated using triangulation. In the description below, the body movement means that the body of a subject or part (referred to as a portion) of the body moves. According to the present embodiment, blood pressure measurement is performed such that the posture of the subject is the posture of a supine or prone position, a sitting position or a standing position. If the posture changes due to a body movement during the measurement period, the height of the position of the heart and the height of the position of the blood pressure measuring device are measured, and height correction is performed such that a measured blood pressure value is approximated to a blood pressure value measured at the position of the heart. According to the present embodiment, the positional relationship between two receivers and one transmitter defines a triangle, and if two or more sets of such triangles are formed, the postures of a supine or prone position, a sitting position and a standing position are applicable.

In the present embodiment, a wrist type blood pressure measurement device to be worn on the wrist will be mentioned as an example of a measurement device (measurement instrument) attached to a person (subject) to be measured, and the wrist type blood pressure measurement device will be hereinafter referred to as a blood pressure measurement device 3. Needless to say, a measurement device which can be provided with a height correction device is not limited to the blood pressure measuring device. The height correction device can be provided for various devices as long as those devices are measurement devices that require updating of height correction due to the presence or absence of a body movement or position change or requires adjustment of measurement timing. That is, the height correction device can be provided for a measurement system that is not limited to the blood pressure measurement system.

The blood pressure measurement system 1 is roughly divided into a height correction device 2 and a blood pressure measurement device 3. The height correction device 2 includes a height correction device main body 20, a first body movement sensor 4 (first sensor), an attachment position transmitter 5, a second body movement sensor 6 (second sensor), a reference position transmitter 7, a first receiver 8 and a second receiver 9. The height correction device 2 according to the present embodiment is constituted by elements excluding the blood pressure measurement device 3 shown in FIG. 1.

In the present embodiment, the blood pressure measurement device 3, the attachment position transmitter 5 and the second body movement sensor 6 are integrally formed adjacent to each other, and are housed in connected casings or a single casing as a second measurement unit 10. Further, the first body movement sensor 4 and the reference position transmitter 7 are integrally formed as a first measurement unit 11.

The second body movement sensor 6 of the present embodiment is worn on the wrist of the subject 100 as a second measurement unit 10 integrally with the blood pressure measurement device 3 and the attachment position transmitter 5. The second body movement sensor 6 detects whether or not there is a body movement that occurs when the wrist or forearm is moved. At least a change in the height of the wrist is detected. The attachment position transmitter 5 transmits a signal indicating that the position of the blood pressure measurement device 3 changes. The first body movement sensor 4 of the present embodiment is worn on the position indicative of the height of the heart of the subject 100, for example, the side under the armpit if the subject 100 is the supine position, integrally with the reference position transmitter 7 as the first measurement unit 11. In this wearing example, the subject may turn sideways from the supine position or the prone position by rolling over during sleep, and it is preferable to additionally arrange the first body movement sensor 4 on the chest in order to detect the position of the heart when the subject lies sideways. That is, it is preferable that two first body movement sensors 4 are arranged near the heart such that one of the first body movement sensors 4 is arranged in the thickness direction (the side) of the body and the other first body movement sensor 4 is arranged in the width direction of the body (the chest). The first body movement sensors 4 detect, as body movement information, the presence or absence of body movement of the upper body of the subject 100 when the subject 100 rolls over. The reference position transmitter 7 transmits a signal indicating that the reference position, i.e., the position of the heart, has moved, that is, the height of the heart has changed.

As a means for arranging the first measurement unit 11 in the vicinity of the heart, for example, a stretchable belt (not shown) to be wound around the chest of the subject 100 is used. At least two attachment devices to which the first measurement units 11 are detachably attachable and which are movable on the belt are provided for the belt, so that at least two first measurement units 11 are properly arranged near the heart in accordance with the physical constitution of the subject 100. Other than the belt, the first measurement units 11 may be attached to a thin vest-type garment (a short sleeveless jacket).

The first and second body movement sensors 4 and 6 constitute a detection unit that detects the presence or absence of a movement (a body movement) occurring in a portion of the body of the subject 100 to be measured 100, using, for example, 3-axis acceleration sensors, namely, a detection unit that detects a height change occurring at least in the portions where the body movement sensors are disposed. As the 3-axis acceleration sensors, semiconductor piezoresistive 3-axis acceleration sensors, capacitive 3-axis acceleration sensors or the like can be used, which are manufactured using known semiconductor technology or MEMS technology. The reason why the 3-axis acceleration sensors are used in the present embodiment is that when the subject rolls over, the body of the subject not only vertically reverses, including rotation of the wrist, but also changes in position both vertically and horizontally, depending upon how the arms swing, and this movement is detected in three directions. Therefore, by using the 3-axis acceleration sensors, not only information on the height direction but also information on the three directions in which the body movement occurs actually can be used, depending upon the method in which detection signals are processed.

The first and second body movement sensors 4 and 6 transmit a body movement occurrence signal indicative of the occurrence of a body movement to a measurement timing setting unit 24 (described later) of the height correction device main body 20. Further, the attachment position transmitter 5 transmits an attachment position signal to the first receiver 8 and the second receiver 9 at timings determined in accordance with the control of the measurement timing setting unit 24. Simultaneously or successively, the reference position transmitter 7 transmits a reference position signal to the first receiver 8 and the second receiver 9 at timings determined in accordance with the control of the measurement timing setting unit 24.

As shown in FIG. 3, the first receiver 8 and the second receiver 9 are located above the head of the subject 100 when the subject 100 is lying on the bed 12 (the supine position, prone position or sideways position), and are arranged on a wall 13 in such a manner as to provide a height difference (inter-receiver distance L0) in the gravity direction (or in the vertical direction).

The inter-receiver distance L0, i.e., the height difference mentioned above, is a known distance (fixed value) determined beforehand. In the present embodiment, the first receiver 8 is arranged on the upper side, the second receiver 9 is arranged on the lower side, and the first measurement unit 11 and the second measurement unit 10 are attached to the subject 100 such that triangles are defined with these elements as vertexes. In this arrangement example, the first receiver 8 and the second receiver 9 can respectively receive an attachment position signal transmitted by the attachment position transmitter 5 attached to the subject 100 and a reference position signal transmitted by the reference position transmitter 7.

The attachment position transmitter 5 and the reference position transmitter 7 are arranged at positions such that as shown in FIG. 4, one triangle is formed by the attachment position transmitter 5, the first receiver 8 and the second receiver 9, and another triangle is formed by the reference position transmitter 7, the first receiver 8 and the second receiver 9.

If the bed 12 is provided with a metallic handrail 14, such as that used in hospitals and the like, a communication failure due to the handrail 14 has to be avoided by arranging the first receiver 8 and the second receiver 9 at positions higher than the handrail 14. The first receiver 8 is arranged higher than the second receiver 9, and where the inter-receiver distance L0 is long, the positions of the attachment position transmitter 5 and the reference position transmitter 7 can be easily detected, and the accuracy also increases. The inter-receiver distance L0 may be, for example, 1 m or more. In the present embodiment, the wall 13 is mentioned as an example of an installation place for which the receivers are provided. Where a patient's blood pressure is measured in a hospital room or the like, the first and second receivers 8 and 9 may be provided for a tall cabinet arranged at the side of the bed. Furthermore, the first and second receivers 8 and 9 may be provided on the ceiling surface directly above the bed on which the subject lies, such that they are spaced by a known interval.

The attachment position transmitter 5 and the reference position transmitter 7 both use wireless communications, and transmit an attachment position signal and a reference position signal for generating height information to each of the first receiver 8 and the second receiver 9. Specifically, the first receiver 8 receives the reference position signal transmitted by the reference position transmitter 7 as a first reference position signal, and similarly, the second receiver 9 receives the reference position signal as a second reference position signal. The first reference position signal and the second reference position signal will be referred to as first position information signals. Also, the first receiver 8 receives the attachment position signal transmitted by the attachment position transmitter 5 as a first attachment position signal, and similarly, the second receiver 9 receives the attachment position signal as a second attachment position signal. The first attachment position signal and the second attachment position signal will be referred to as second position information signals.

In order to generate highly accurate height information, it is necessary to form a triangle, using accurate position information. Therefore, the attachment position signal and the reference position signal have to be transmitted simultaneously or successively such that there is not an interval between the transmission timings of the attachment position signal and the reference position signal. Where simultaneous transmission and reception are performed, the attachment position transmitter 5 and the reference position transmitter 7 have to use communication signals of different frequencies.

With respect to the communication method, where the cell-ID method used for PHS communications is applied, the first receiver 8 and the second receiver 9 are used as base stations, and the attachment position transmitter 5 and the reference position transmitter 7 associated with them by wireless communications are used as wireless terminals. Other than this, a radio wave arrival time difference method (TDOA: Time Difference of Arrival) used by the GPS system, CDMA mobile phones or Wi-Fi terminals, or a radio wave received signal strength method (RSSI: Received Signal Strength Indicator) used by PHS or Bluetooth (registered trademark) can be used. If BLE (Bluetooth Low Energy) is used as a protocol of near field communications, communications can be performed with extremely low power. If a clock time is incorporated in the transmitted signals, synchronization with the generation timings of information of various devices (such as the activation time and stop time of a sensor signal) can be performed at the time of information processing. Needless to say, the communication means is not limited to wireless communications, and communications that use sound waves instead of wireless signals, for example, ultrasonic communications, may be performed.

Next, the blood pressure measurement device 3 will be described with reference to FIG. 2.

The blood pressure measurement device 3 mainly includes a cuff 31 for applying pressure to the blood vessel of the subject 100, an air pump 32 for supplying gas (air), a valve 33 for supplying air from the air pump 32 to the cuff 31 and exhausting air from the cuff 31 to the outside, a pressure sensor 34 for measuring an internal pressure of the cuff and a blood pressure, and a control unit (CPU) 35 for controlling the entire device and performing blood pressure measurement. Further, the blood pressure measurement device 3 includes a display unit 36 for displaying the detected blood pressure information and operation contents, an operation unit 37 including operation buttons and a touch panel for performing measurement setting and entering various inputs, an input/output unit 38 for performing communications with an external device, such as the height correction device main body 20, to input blood pressure measurement execution instructions for height correction and to output blood pressure information, and a power supply 39 consisting of a rechargeable battery, a primary battery, or the like.

The blood pressure measurement device 3 has a known configuration, but in addition to the normal measurement of blood pressure measured at predetermined constant intervals, the measurement timing setting unit 24 sets timings at which a blood pressure is irregularly measured immediately after the body movement of the subject 100 occurs and the height correction value is updated.

Next, the height correction device main body 20 will be described with reference to FIG. 1.

The height correction device main body 20 mainly includes a height information generation unit 21, a height correction value calculation unit 22, a processing unit (CPU) 23, a measurement timing setting unit 24, an input unit 25, a display unit 26, a memory 27 and an interface (I/F) unit 28. Although no power supply is illustrated, a power supply unit (battery) may be provided independently, or the power supply 39 of the blood pressure measurement device 3 may be utilized.

In this configuration, the height information generation unit 21 generates first height information, described later, from the first position information signals (the first reference position signal and the second reference position signal) transmitted from the reference position transmitter 7 and received by the first receiver 8 and the second receiver 9.

Next, the height information generation unit 21 generates second height information, described later, from the second position information signals (the first attachment position signal and the second attachment position signal) transmitted from the attachment position transmitter 5 and received by the first receiver 8 and the second receiver 9.

The height correction value calculation unit 22 calculates a height correction value for a blood pressure value measured by the blood pressure measurement device 3, based on the first and second height information generated by the height information generation unit 21. Since blood is a liquid, it is usually under the influence of gravity, and the pressure with which the heart functioning as a blood pump supplies the blood, that is, the blood pressure, also fluctuates. Where the measurement position is away from the heart in the height direction (gravity direction), the measured blood pressure value contains a measurement error. In general, the measured blood pressure value decreases as the measurement position is more away and higher than the heart, and increases as the measurement position is more away and lower than the heart. The correction value is a correction value that eliminates or reduces the measurement error attributable to the height difference, and corrects the measured blood pressure value such that it is approximated to a blood pressure value measured near the heart.

The processing unit 23 performs control of the entire apparatus and control of communications, and performs correction processing on a blood pressure value input from the blood pressure measurement device 3, using a height correction value. That is, the processing unit 23 performs height correction on a blood pressure measurement value acquired by the blood pressure measurement device 3, approximates it to a measurement value measured at the same height position as the heart, and thereby generates a highly accurate measurement value.

The input unit 25 is constituted by operation buttons used for determining settings, a touch panel, etc. The display unit 26 displays information necessary for correcting such as the correction value and the like, information on communications, a corrected blood pressure value, and the like. The memory 27 rewritably stores information necessary for the correction operation, the calculated height correction value, etc. The interface (I/F) unit 28 transmits a blood pressure value measured and subjected to height correction and information on the blood pressure value to an administrator's personal computer or server connected via a network such as a LAN. Needless to say, the blood pressure value subjected to height correction can be sent back to the blood pressure measurement device 3 and displayed on the display unit 36.

Next, a description will be given of how a height correction value is calculated by the height correction device main body 20. According to the present embodiment, the position detection using communications can use an estimation method of the position estimation technology (AOA: Angle of Arrival) and triangulation (see Tomoaki OHTSUKI, "Position Estimation Technology", IEICE Technical Report, the Institute of Electronics, Information and Communication Engineers).

As shown in FIG. 4, the first receiver 8, the second receiver 9 and the attachment position transmitter 5 form a triangle whose vertices are defined by them, and the first receiver 8, the second receiver 9 and the reference position transmitter 7 form a triangle whose vertexes are defined by them. By using a triangle of which at least one side (the inter-receiver distance L0) is known, the distances from the wall 13 to the attachment position transmitter 5 and the reference position transmitter 7 and the coordinates can be calculated based on known triangulation techniques and sine theorem.

First, since the first receiver 8 and the second receiver 9 are provided on the wall 13 and their heights and one side (inter-receiver distance L0) are known, their positions (coordinates) are known. The first receiver 8 and the second receiver 9 detect arrival directions in which attachment position signals, wireless signals, come from the attachment position transmitter 5 (incident angles $\alpha1$ and $\beta1$ of the wireless signals). Similarly, arrival directions in which reference position signals, wireless signals, come from the reference position transmitter 7 (incident angles $\alpha2$ and $\beta2$ of the wireless signals) are detected.

Further, by using the sine theorem, distances L1 from the first receiver 8 and the second receiver 9 to the reference position transmitter 7 and first height information P1 (first coordinate information) can be calculated, and distances L2 to the attachment position transmitter 5 and second height information P2 (second coordinate information) can be calculated. Height difference h, which is height information, can be obtained by subtracting the calculated second height information P2 from the calculated first height information P1, which is reference information. By using the generally known adjustment (hydrostatic pressure) of 0.7 mmHg (mercury column) for the 1 cm difference, a height correction value for performing correction that excludes the influence of the height can be calculated from the height difference h such that the measured blood pressure can be approximated to a blood pressure value measured at the height of the heart. For example, where the wrist on which the blood pressure measurement device 3 is worn is higher than the heart and the height difference h is 5 cm, 3.5 mmHg has to be added for correction to the blood pressure measurement value measured by the blood pressure measurement device 3. In this case, with respect to the blood pressure value measured by the blood pressure measurement device 3, a numerical value determined by the height difference h is used as a height correction value.

The height correction value obtained from the height difference h is stored in the memory 27. Each time the first and second body movement sensors 4 and 6 detect a body movement of the subject 100, the first receiver 8 and the second receiver 9 transmit position information signals, and a new height correction value is calculated and stored in the memory 27 as an update value. In a first measurement method described later, in addition to blood pressure measurement performed at predetermined intervals in time series, blood pressure measurement may be performed immediately after the height correction value is updated, and a record is made of a movement of the subject 100.

Therefore, blood pressure measurement values obtained by the blood pressure measurement performed after a body movement of the subject occurs and the height correction value is updated are recorded between blood pressure measurement values which the blood pressure measurement device acquires in time series and at regular intervals, i.e., predetermined intervals set in advance. Therefore, it can be confirmed at which time (a point of time) the body movement occurs. Alternatively, as a second measurement method, blood pressure measurement may be performed only at the start of measurement and at the time of updating the height correction value. According to this measurement method, power consumption can be reduced.

Figure 5:
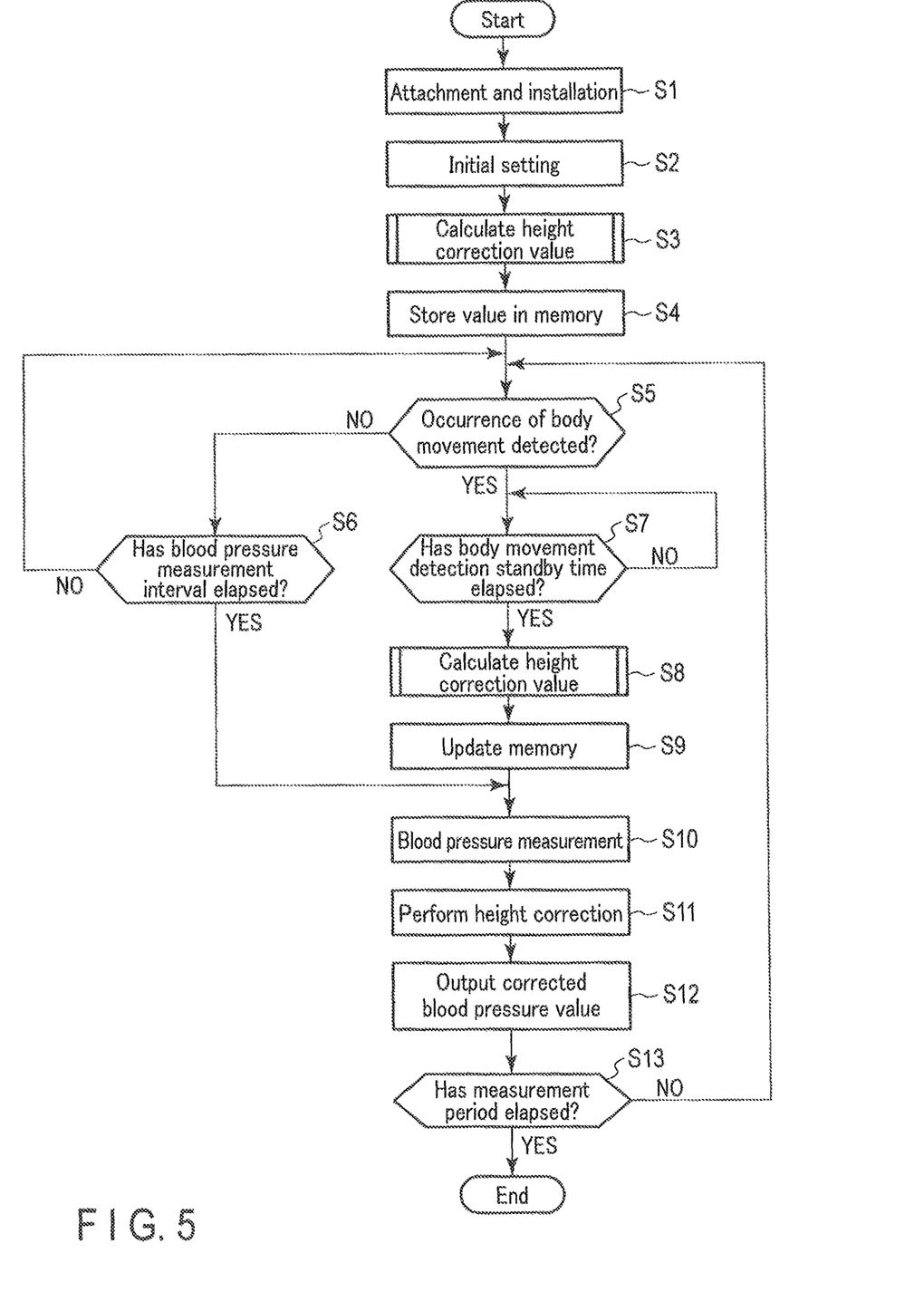
FIG. 5 is a flowchart for illustrating a measurement procedure of the blood pressure measurement system.

Next, the measurement procedure of the blood pressure measurement system 1 will be described with reference to the flowchart shown in FIG. 5.

First, the first measurement unit 11 and the second measurement unit 10 are attached to the subject 100 who is sleeping state in the supine posture as shown in FIG. 3, and the first receiver 8 and the second receiver 9 are installed on the wall 13 (step S1). Specifically, the first measurement unit 11 is attached to the side of the subject 100 under the armpit such that it is around the same height as the heart from the floor surface, and the second measurement unit 10 including the blood pressure measurement device 3 is attached to the wrist of the subject 100.

As an attachment means of these measurement units, a belt provided with a dedicated attachment tool such as a unit attachment holder may be used for fixing, or an adhesive tape or the like may be used for fixing. When the two first measurement units 11 are attached, at least two movable holders are provided on the belt worn around the chest, and the holders are moved to the chest and armpit side near the heart in accordance with the physical constitution of the subject such that the measurement units 11 are placed at proper positions. The blood pressure measurement device 3 is attached such that the cuff 31 can properly press the blood vessel. As shown in FIG. 3, the first receiver 8 is arranged on the wall 13 located on head side at a position higher than the head of the subject 100, and the second receiver 9 is arranged at a lower position, with an inter-receiver distance L0 maintained. In order to facilitate the arrangement, the first receiver 8 and the second receiver 9 may be fixed to a base member (not shown) with the inter-receiver distance L0 maintained. In this case, the base member is hung on the wall.

Next, initial setting is performed (step S2). In this initial setting, the blood pressure measurement device 3 is activated to perform zero adjustment, and, for example, setting of a blood pressure measurement period, a blood pressure measurement interval (or the number of measurements), etc. is performed. Further, the measurement timing setting unit 24 sets a body movement detection standby time, described later, a blood pressure measurement instruction to be supplied to the blood pressure measurement device 3, and the like. After this initial setting, measurement is started automatically or after a start instruction is issued from the operation unit 37 of the blood pressure measurement device 3 or the input unit 25 of the height correction device 2. Simultaneous with the start of this measurement, the height difference h between the attachment position transmitter 5 and the reference position transmitter 7 is detected according to a subroutine for calculating a height correction value described later, and a height correction value (initial value) is determined (step S3). Then, the determined height correction value (initial value) is stored in the memory 27 (step S4).

After the height correction value (initial value) is determined, the first body movement sensor 4 and the second body movement sensor 6 detect whether or not a body movement of the subject 100 occurs after the start of measurement, and the first body movement sensor 4 and the second body movement sensor 6 output a detection signal to the height information generation unit 21 of the processing unit 23 (step S5). If a body movement is not detected in the first body movement sensor 4 or the second body movement sensor 6 (NO), the processing unit 23 determines whether a set blood pressure measurement interval has elapsed (step S6). If it is determined in step S6 that the blood pressure measurement interval has elapsed (YES), the process proceeds to step S10, described later, and the blood pressure measurement device 3 performs blood pressure measurement. On the other hand, if it is determined that the blood pressure measurement interval has not elapsed (NO), the process returns to step S5, and the first body movement sensor 4 and the second body movement sensor 6 continue to detect whether or not a body movement occurs.

Where the first body movement sensor 4 and/or the second body movement sensor 6 detect a body movement of the subject 100 in the body movement detection of step S5 (YES), the first body movement sensor 4 and/or the second body movement sensor 6 output a detection signal continuously to the processing unit 23 while the body movement is occurring. The processing unit 23 determines whether or not the body movement detection standby time set in advance has elapsed after the end of the reception of the detection signal (step S7). Since it can be assumed that the subject 100 continues to move the body (for example, when the subject rolls over, the shoulder may turn and the wrist may move to the opposite right or left side), determination is made as to whether or not the body movement detection standby time set in advance has elapsed at the end of the body movement. In this example, the count of the body movement detection standby time is started at the end of the body movement, but the count may be started at the start of the body movement.

If it is determined that the body movement detection standby time has elapsed (YES), the height correction value calculation unit 22 detects a height difference h between the attachment position transmitter 5 and the reference position transmitter 7 according to a subroutine for calculating a height correction value described later, and calculates a height correction value (step S8). Then, the processing unit 23 updates the height correction value stored in the memory 27 (step S9).

After the height correction value is updated, the blood pressure measurement device 3 performs blood pressure measurement in response to a blood pressure measurement instruction supplied from the measurement timing setting unit 24 (step S10). The processing unit 23 performs height correction on the measured blood pressure value in accordance with the height correction value read from the memory 27 (step S11). The corrected blood pressure value is transmitted from the interface (I/F) unit 28 to the administrator's personal computer or server connected via the LAN (step S12). Alternatively, the corrected blood pressure value may be transmitted to the blood pressure measurement device 3 and displayed on the display unit 36. It is determined whether or not the blood pressure measurement period set at the time of initial setting has elapsed (step S13). If this determination shows that the blood pressure measurement period has elapsed (YES), a series of measurements are ended. If the determination shows that the blood pressure measurement period has not elapsed (NO), the process returns to step S5, and the blood pressure measurement is continued. Where the blood pressure measurement period is not set, the measurer stops the blood pressure measurement.

Figure 6:
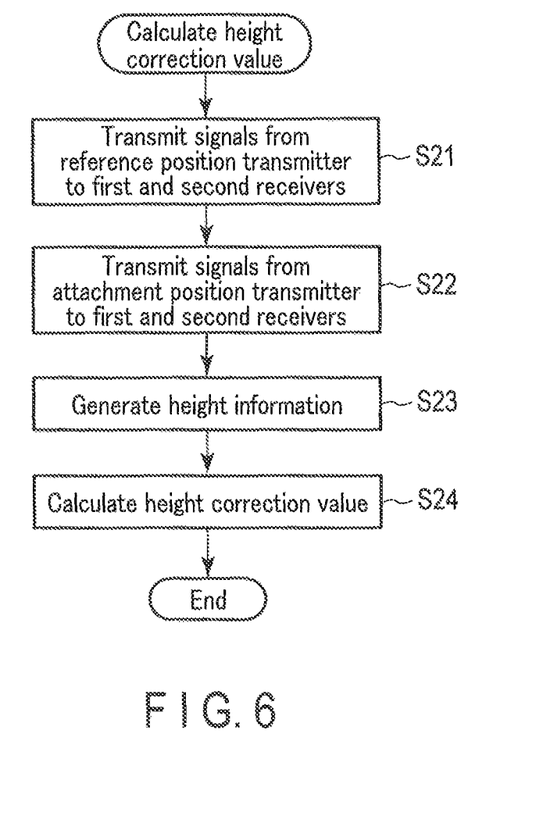
FIG. 6 is a flowchart for illustrating a subroutine of the height correction value calculation shown in FIG. 5.

Next, with reference to the flowchart shown in FIG. 6, a description will be given of how the calculation procedure is performed according to the subroutine of calculating the height correction value in step S3 or S8 shown in FIG. 5.

In this subroutine, the reference position transmitter 7 first transmits a first reference position signal and a second reference position signal (first position information signals) preset in advance to the first and second receivers 8 and 9 (step S21), after the initial setting is performed in step S2 mentioned above or after the elapse of the body movement detection standby time is detected in step S7.

Immediately after the transmission, the attachment position transmitter 5 transmits a first attachment position signal and a second attachment position signal (second position information signals) to the first and second receivers 8 and 9 (step S22). Where the carrier waves of the reference position signals and the attachment position signals are different, the signals may be simultaneously transmitted and received, and are then processed by the first and second receivers 8 and 9.

The first and second receivers 8 and 9 respectively receive the first reference position signal and the second reference position signal (first position information signals) from the reference position transmitter 7, also respectively receive the first attachment position signal and the second attachment position signal (second position information signals) from the attachment position transmitter 5, and output these position information signals to the height information generation unit 21. The height information generation unit 21 receives these position information signals and generates a height difference h, which is height information (step S23). That is, the height information generation unit 21 generates the height difference h from the first height information P1 and the second height information P2, as described above.

Next, the height correction value calculation unit 22 calculates a height correction value for correcting the measured blood pressure value from the height difference h (step S24), and the subroutine for calculating the height correction value ends. Thereafter, in the case of the subroutine of step S3, the process proceeds to step S5. In the case of the subroutine of step S8, the process proceeds to step S9, the processing unit 23 updates the height correction value stored in the memory 27, and the blood pressure measurement device 3 performs the blood pressure measurement after the correction value is updated in step S10.

As described above, according to the present embodiment, when the body of a subject rotates or moves at the position where the measurement device is attached, during the measurement period including the sleep period, height information on the reference position of the body and height information on the attachment position are measured using communication technology, and the obtained measurement values are subjected to height correction using reference height information and are approximated to measurement values measured at the height of the reference position, to thereby obtain highly accurate measurement values.

Even if the subject sleeping in a supine or prone position unconsciously rolls over or swings the arm, the blood pressure measured by the blood pressure measurement device 3 is always corrected and approximated to the blood pressure value obtained at the height of the heart, so that the measurement error can be reduced and an accurate blood pressure value can be obtained. Every time the body moves, blood pressure measurement is performed after the end of the movement. It is therefore possible to clearly confirm whether the change in blood pressure value is due to the body movement or due to a reason other than the body movement. Thus, misdiagnosis can be eliminated and blood pressure values can be made to contribute to accurate diagnosis.

The measurement unit including the body movement sensor and the transmitter can be integrated with the blood pressure measurement device, so that the measurement unit can be easily attached to or detached from such a portion of the subject as the wrist.

The belt or vest provided with at least two attachment devices for which second measurement units movable on the belt are removably provided is wound around the chest of the subject. Since the two second measurement units can be moved in accordance with the physical constitution of the subject, they can be properly positioned near the heart, and attachment and detachment are easy.

Furthermore, size reduction can be realized as compared with a conventional height correction sensor using the water head pressure of a tube. Compared with the configuration in which body portions of the subject are connected by a tube, the restriction on the movement of the body is reduced even in the measurement performed for a long time, the burden on the subject is reduced, and the feeling of discomfort can be reduced.

In addition, since blood pressure measurement is performed periodically at set time intervals, the consumption of a power source such as a battery can be suppressed.

[Second Embodiment]

Figure 7:
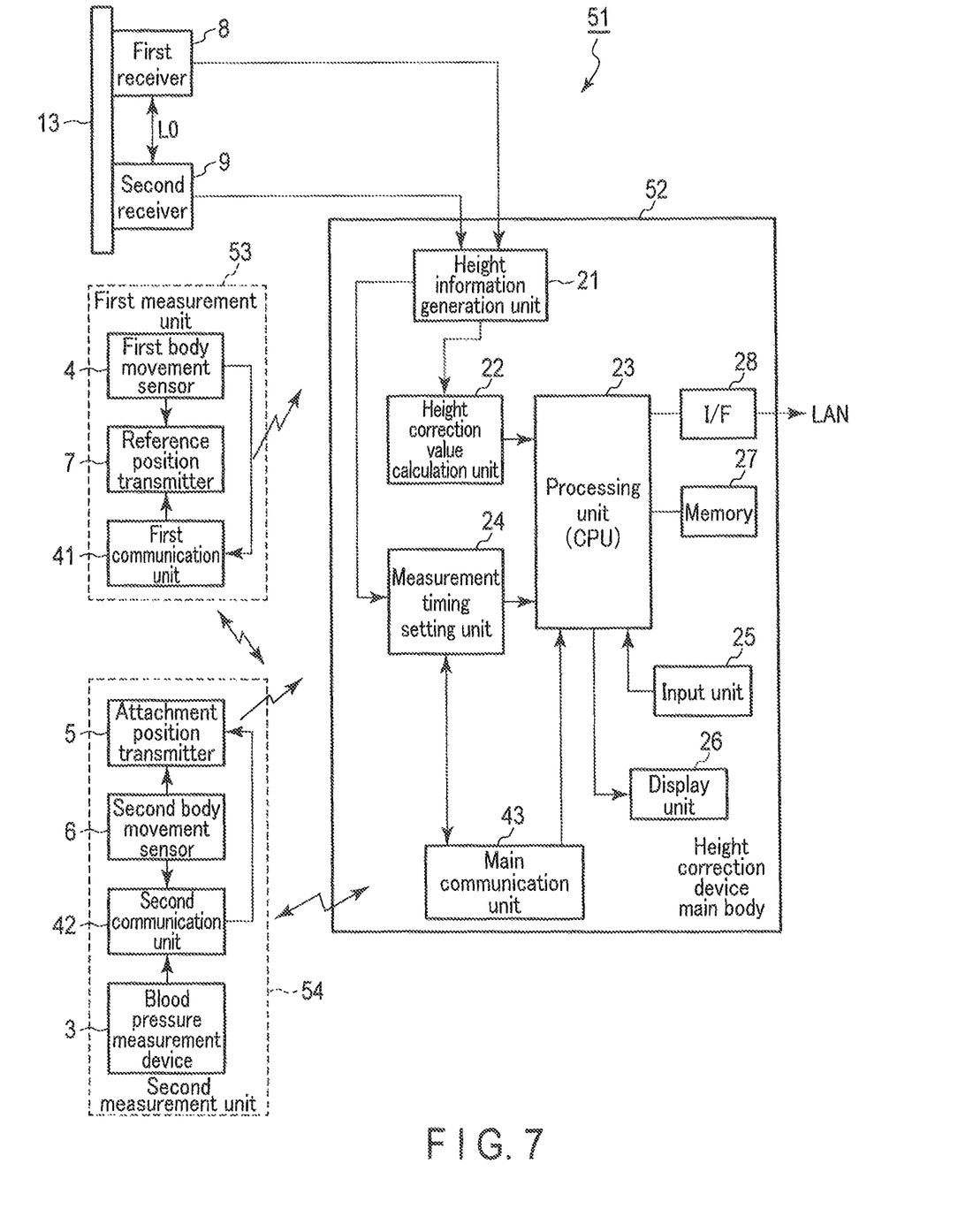
FIG. 7 is a block diagram showing a configuration example of a blood pressure measurement system using a height correction device according to a second embodiment.

Next, a blood pressure measurement system using a height correction device according to the second embodiment will be described. FIG. 7 is a block diagram showing a configuration example of a blood pressure measurement system 51 using a height correction device main body 52 according to the second embodiment. In the first embodiment described above, the measurement timing setting unit 24 connected by wire is used to control the transmission timings of the reference position transmitter 7 and the attachment position transmitter 5. In the second embodiment, wireless connection is used and each unit is isolated. That is, the first measurement unit 53 and the second measurement unit 54 are configured to transmit and receive information to and from the height correction device main body 52 by wireless communications. Further, a blood pressure (blood pressure information) measured by the blood pressure measurement device 3 is transmitted to the height correction device main body 52 by wireless communications to carry out height correction. In the description of the present embodiment, the structural elements similar to those of the first embodiment (FIGS. 1 and 2A) described above will be denoted by the same reference symbols as those used for the first embodiment, and a detailed description will be omitted. The communication signals are wireless or not, and the information to be propagated is the same.

The first measurement unit 53 of the blood pressure measurement system 51 of the present embodiment includes a first communication unit 41 that performs wireless communications, in addition to the first body movement sensor 4 and the reference position transmitter 7. The second measurement unit 54 includes a second communication unit 42 that performs wireless communications, in addition to the blood pressure measurement device 3, the second body movement sensor 6 and the attachment position transmitter 5. In the height correction device main body 52, a main communication unit 43 that performs wireless communications with the first communication unit 41 and the second communication unit 42 is provided in addition to the elements described above. That is, the main communication unit 43 of the height correction device main body 52 wirelessly communicates with the first communication unit 41 of the first measurement unit 53 and the second communication unit 42 of the second measurement unit 54.

First, the first communication unit 41 and the second communication unit 42 convert a body movement generation signal, supplied from the first body movement sensor 4 and the second body movement sensor 6 and indicative of the occurrence of a body movement of the subject, into a wireless signal and transmit the wireless signal to the main communication unit 43 of the height correction device main body 52.

Next, the main communication unit 43 outputs the received body movement generation signal to the measurement timing setting unit 24. The measurement timing setting unit 24 transmits an instruction signal, which instructs simultaneous transmission or successive transmission of a reference position signal and an attachment position signal, from the main communication unit 43 to the first communication unit 41 and the second communication unit 42.

Further, the first communication unit 41 and the second communication unit 42 output a transmission instruction signal to the attachment position transmitter 5 and the reference position transmitter 7. Upon receipt of the transmission instruction signal, the attachment position transmitter 5 and the reference position transmitter 7 respectively transmit a first reference position signal and a second reference position signal (first position information signals), which are wireless signals, and a first attachment position signal and a second attachment position signal (second position information signals) to the first receiver 8 and the second receiver 9, which are arranged away from each other in the vertical direction, simultaneously or successively. The first receiver 8 and the second receiver 9 transmit the received first position information signals and second position information signals to the height information generation unit 21. The height information generation unit 21 generates the above-described height information (height difference h) from these position information signals. The height correction value calculation unit 22 calculates a height correction value for the blood pressure value measured by the blood pressure measurement device 3, based on the height information generated in the height information generation unit 21. The calculated height correction value is temporarily stored in the memory 27. Each time measurement is performed before the height correction value is updated in response to the next body movement, the calculated height correction value is read by the processing unit 23 and used for the height correction on a blood pressure value measured by the blood pressure measurement device 3.

The blood pressure subjected to the height correction is transmitted from the interface unit 28 to the administrator's personal computer or server via the network. In addition, the blood pressure subjected to the height correction can be transmitted, as a wireless signal, to the blood pressure measurement device 3 via the second communication unit 42, and the blood pressure subjected to the height correction can be displayed on the display unit 36.

The present embodiment provides the same advantages as achieved by the first embodiment described above. In addition, in the height correction device, the first measurement unit 53 and second measurement unit 54 worn on the body of the subject (the chest (near the heart) and the wrist) communicate transmission instructions and position information signals by wireless. Since the height correction device has a cordless configuration which does not employ signal lines required in the conventional art, all factors that disturb the movement of the subject are eliminated. Even when measurement is performed for a long time, an uncomfortable feeling is not caused during operation due to signal lines, and the feeling of discomfort can be remarkably reduced.

[Third Embodiment]

Figure 8A:
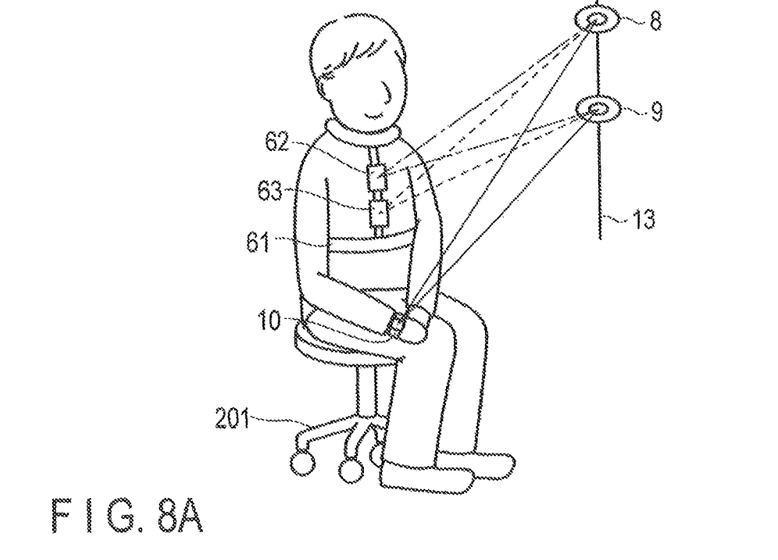
FIG. 8A is a view conceptually showing how arrangement positions of a transmitter and a receiver of the height correction device are according to a third embodiment when the subject is in a sitting posture.
Figure 8B:
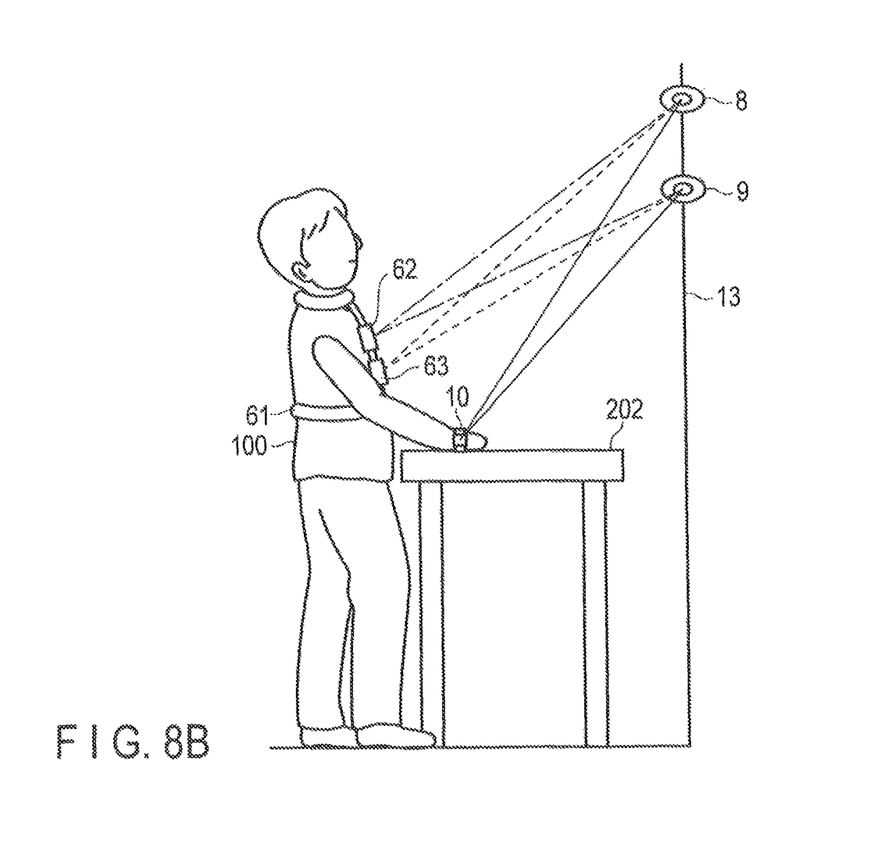
FIG. 8B is a view conceptually showing how arrangement positions of the transmitter and the receiver of the height correction device are according to the third embodiment when the subject is in a standing position.

Next, a blood pressure measurement system using a height correction device according to the third embodiment will be described. FIG. 8A is a view conceptually showing how arrangement positions of a measurement unit, i.e., a transmitter of a height correction device, and a receiver are when the subject is in a sitting posture. FIG. 8B is a view conceptually showing how arrangement positions of the transmitter, i.e., the measurement unit of the height correction device, and the receiver are when the subject is in a standing position. In the first and second embodiments described above, the posture of the subject was described as sleeping on the floor base in the supine position. In the third embodiment, the arrangement of the transmitters is changed such that it is applicable to the state where the subject is in a sitting or standing posture, with the upper body lifted.

In FIG. 8A, the subject 100 is seated on a chair 201 and is in a sitting position, with the upper body raised vertically. A first A measurement unit 62 and a first B measurement unit 63, which correspond to the first measurement unit 1 of the height correction device, are configured by a transmitter and a body movement sensor, as described above. The first A measurement unit 62 and the first B measurement unit 63 are arranged such that they sandwich the heart of the subject, with the heart at the center. These measurement units 62 and 63 are movable on belt-like wearing clothes 64 such that they can be positioned with reference to the heart of the subject, and are fixed by a stopper (not shown) or the like.

Since the first A measuring unit 62 and the first B measuring unit 63 are only required to sandwich the heart at the center between them, the wearing clothes 64 are not necessarily needed, and the first A measuring unit 62 and the first B measuring unit 63 may be attached to the clothes of the subject by means of an adhesive tape or the like.

A second measurement unit 10 including a blood pressure device 3 similar to that described above is attached to the wrist of the subject. The receivers 8 and 9 are arranged on a wall (not shown) such that they are away from each other in the vertical direction.

In the present embodiment as well, as shown in FIG. 8, three triangles are formed such that the receivers 8 and 9 are two shared vertices and each of the second measurement unit 10, the first A measurement unit 62 and the first B measurement unit 63 is one vertex. As described above, the distances from the wall 13 to the second measurement unit 10, the first A measurement unit 62 and the first B measurement unit 63 and locations expressed by coordinates can be calculated by using known triangulation techniques and sine theorem for these triangles. In the present embodiment, the first A measurement unit 62 and the first B measurement unit 63 are arranged such that they sandwich the heart at the center between them, so that the height of the heart of the subject is regarded as being represented by an average value between the first A measurement unit 62 and the first B measurement unit 63. When the heart cannot be at the center, a distance ratio between the distances from the heart to the first A measurement unit 62 and the first B measurement unit 63 may be used. By calculating a difference between the average value and the height of the position of the second measurement unit 10, a height correction value used for correcting a blood pressure difference caused by the action of gravity is calculated.

FIG. 8B shows that the subject is in a standing position, with the hand wearing the second measurement unit 10 being placed on the table. In FIG. 8B, structural elements similar to those shown in FIG. 8A are denoted by the same reference symbols, and a description thereof will be omitted. With respect to the posture in the standing position, a height correction value can be obtained in the same way as the seated position described above.

The present embodiment has advantages similar to those of the first and second embodiments described above. In addition, with respect to not only the postures in the supine and prone positions but also the posture in a seated position on a chair and the posture in a standing posture, blood pressure values equivalent to those measured at the heart position can be measured.

The present invention is not limited to the above-mentioned embodiments and can be reduced to practice by modifying the elements without departing from the spirit and scope of the invention. In addition, the embodiments may be implemented by combining them as appropriate, in which case combined advantages are obtainable. Furthermore, the above-described embodiments include various inventions, and a variety of inventions can be derived by selectively combining structural elements disclosed in connection with the embodiments. For example, if the object is achieved and the advantages are attained even after some of the structural elements disclosed in connection with the embodiments are deleted, the structure made up of the remaining structural elements can be extracted as an invention.

[Additional Notes]

(1) A height correction device comprising:
a reference position transmitter that transmits a height of a reference position as a first position information signal;
an attachment position transmitter that transmits a height of an attachment position of a measurement device as a second position information signal;
a first sensor that detects a variation in the reference position transmitter;
a second sensor that detects a variation in the attachment position transmitter;
a first receiver arranged higher than the reference position transmitter and the attachment position transmitter in a direction of gravity;
a second receiver that is spaced apart from the first receiver by a predetermined distance and arranged at such a height position as to form a triangle such that the first receiver is a first vertex, the attachment position transmitter or the reference position transmitter is a second vertex, and the height position is a third position;
a height information generation unit that obtains first height information on the reference position transmitter from first position information signals received by the first receiver and the second receiver, that obtains second height information on the attachment position transmitter from second position information signals received by the first receiver and the second receiver, and that calculates a height difference from a difference between the first height information and the second height information;
a height correction value calculation unit that calculates a height correction value in accordance with the height difference, so as to correct a measurement error caused by action of the gravity; and
a processing unit that calculates the height difference and updates the height correction value each time a height variation is detected by the first sensor and the second sensor, and that corrects a measurement result measured by the measurement device in accordance with the height correction value, so as to approximate the measurement result to a measurement result measured at the height of the reference position.

(2) A height correction device comprising:
a reference position transmitter that is attached at a height of a position of a heart of a subject in a sleeping state, and that transmits a first position information signal indicative of the height of the heart;
an attachment position transmitter that is attached integrally with a movable external blood pressure measurement device and that transmits a second position information signal indicative of a height of an attachment position of the blood pressure measurement device;
a first sensor that is provided integrally with the reference position transmitter and that detects a variation in the height of the position of the heart;
a second sensor that is provided integrally with the attachment position transmitter and that detects a variation in the height of the position of the blood pressure measurement device;
a first receiver arranged higher than the heart and the attachment position of the blood pressure measurement device in a direction of gravity;
a second receiver that is spaced apart from the first receiver by a predetermined distance and arranged at such a height position as to form a triangle such that the first receiver is a first vertex, the attachment position transmitter or the reference position transmitter is a second vertex, and the height position is a third vertex;
a height information generation unit that obtains the height of the position of the heart from the first position information signal, that obtains the height of the attachment position of the blood pressure measurement device from the second position information signal, and that calculates a height difference between the position of the heart and the attachment position;
a height correction value calculation unit that calculates a height correction value to correct a blood pressure measurement error caused by action of the gravity due to the height difference;
a memory unit that stores the height correction value calculated by the height correction value calculation unit; and
a processing unit that calculates the height difference and updates the height correction value each time a height variation is detected by the first sensor and the second sensor, and that corrects a blood pressure measurement value measured by the blood pressure measurement device in accordance with the height correction value, so as to approximate the blood pressure measurement value to a blood pressure value measured at the height of the heart.

The invention claimed is:

1. A height correction device comprising:
a reference position transmitter that transmits a first position information signal indicative of a position of a heart of a subject;
an attachment position transmitter that transmits a second position information signal indicative of an attachment position of an external blood pressure measurement device;
a first sensor that detects a first variation in a height of the position of the heart;
a second sensor that detects a second variation in a height of the attachment position of the blood pressure measurement device;
a first receiver that receives the first position information signal and the second position information signal;
a second receiver that receives the first position information signal and the second position information signal, and that is spaced apart from the first receiver by a predetermined distance; and
processing circuitry coupled to a memory, the processing circuitry configured to
obtain the height of the position of the heart from the first position information signal and obtain the height of the attachment position of the blood pressure measurement device from the second position information signal,
calculate a height difference between the position of the heart and the attachment position,
calculate a height correction value to correct a blood pressure measurement error caused by action of gravity due to the height difference, store the height correction value, and
correct a blood pressure measurement value measured by the blood pressure measurement device in accordance with the height correction value,
wherein the height correction value is calculated based on elapse of a body movement detection standby time from the detection of at least one of the first variation or the second variation.

2. The height correction device according to claim 1, wherein a triangle is formed such that the first receiver is a first vertex, the reference position transmitter or the attachment position transmitter is a second vertex, and the second receiver is a third vertex, and
the processing circuitry is further configured to respectively calculate distance information from the first receiver and the second receiver to the reference position transmitter and the attachment position transmitter, using the triangle, and generate the height difference between the heart and the blood pressure measurement device from coordinate information based on the distance information.

3. The height correction device according to claim 1, wherein the processing circuitry is further configured to
cause the blood pressure measurement device to perform blood pressure measurement, after the at least one of the first variation or the second variation is detected and the height correction value is calculated, and
set the blood pressure measurement which is to be performed by the blood pressure measurement device immediately and always after the height correction value is updated, in addition to the blood pressure measurement which the blood pressure measurement device performs in time series at regular intervals within a preset measurement period.

4. The height correction device according to claim 1, wherein
the first sensor and the reference position transmitter are used at least in pairs, and
the height correction device further comprises:
a belt that is configured to be wound around the subject; and
an attachment device that is movably provided on the belt and that enables the first sensor and the reference position transmitter to be attached.

5. The height measurement device according to claim 1, further comprising;
a first communication unit that is connected to the first sensor and the reference position transmitter, and that converts a body movement occurrence signal detected by the first sensor and an instruction signal instructing the reference position transmitter to transmit a reference position signal into wireless signals for wireless communications; and
a second communication unit that is connected to the blood pressure measurement device, the second sensor and the reference position transmitter, and that converts a measurement timing signal for the blood pressure measurement device, a body movement occurrence signal detected by the second sensor and an instruction signal instructing the attachment position transmitter to transmit an attachment position signal into wireless signals for wireless communications, wherein the processing circuitry is further configured to
cause the blood pressure measurement device to perform blood pressure measurement, after the at least one of the first variation or the second variation is detected and the height correction value is calculated,
perform wireless communications between the first communication unit and the second communication unit, and
communicate the body movement occurrence signal, the reference position signal and the attachment position signal.

6. A blood pressure measurement system comprising:
a wrist type blood pressure measurement device configured to be attached to a wrist of a subject, or an upper arm type blood pressure measurement device configured to be attached to an upper arm; and
a height correction device according to claim 1.

7. A height correction method comprising:
transmitting a height of a reference position as a first position information signal;
transmitting a height of an attachment position of an external measurement device as a second position information signal;
detecting a first variation in the reference position;
detecting a second variation in the attachment position of the measurement device;
receiving the first position information signal and the second position information signal as first reception signals;
receiving the first position information signal and the second position information signal as second reception signals at a position that is away from a reception position of the first reception signals by a predetermined distance;
obtaining the height of the reference position from the first position information signal, obtaining the height of the attachment position of the measurement device from the second position information signal, and calculating a height difference between the reference position and the attachment position of the measurement device;
calculating a height correction value for approximating a measurement value measured at the attachment position of the measurement device to a measurement value measured at the reference position; and
correcting a measurement result measured by the measurement device in accordance with the height correction value, so as to approximate the measurement result to a measurement result measured at the height of the reference position,
wherein
where at least one of the first variation occurring in the reference position or the second variation occurring in the attachment position of the measurement device is detected, the height correction value is calculated based on elapse of a body movement detection standby time from the detection of the at least one of the first variation or the second variation.

* * * * *